United States Patent [19]
Gage et al.

[11] Patent Number: 5,947,972
[45] Date of Patent: Sep. 7, 1999

[54] IRRIGATION PRESSURIZATION SYSTEM

[75] Inventors: Gary B. Gage, Arlington; Glenn T. Carlson, Keller, both of Tex.

[73] Assignee: Midas Rex, L.P., Fort Worth, Tex.

[21] Appl. No.: 09/181,269

[22] Filed: Oct. 28, 1998

[51] Int. Cl.[6] .................................................. A61B 17/56
[52] U.S. Cl. .................. 606/80; 606/79; 408/59
[58] Field of Search ................... 606/79, 80, 81, 606/82, 83, 84, 85, 86, 180; 408/56, 57, 59

[56] References Cited

U.S. PATENT DOCUMENTS 5,569,254  10/1996  Carlson et al. ........................... 606/79
5,730,752   3/1998  Alden et al. ............................ 606/180

*Primary Examiner*—Guy V. Tucker
*Attorney, Agent, or Firm*—Senniger, Powers, Leavitt & Roedel

[57] ABSTRACT

A surgical tool for resecting bone has a pneumatic motor within a tool body which rotates a coaxial tool implement. The tool implement is provided with irrigation fluid from a fluid reservoir. The reservoir and the motor are charged with pressurized air from a pressurized air source. A fluid control valve is located between the reservoir and the tool, and an air control valve is located between the air pressure source and the motor. The air control valve is controlled by a variable foot pedal or hand valve so that the speed of the motor is variably actuated by the foot valve.

16 Claims, 1 Drawing Sheet

IRRIGATION PRESSURIZATION SYSTEM

TECHNICAL FIELD

This invention relates in general to surgical tools for surgical operations and in particular to motorized surgical tools for resecting bones.

BACKGROUND ART

A surgical tool and method for operating the surgical tool are provided for resecting bone. The surgical tool includes a rotary pneumatic motor to which a resecting tool is secured. Irrigation fluid is passed through a flow channel on the surgical tool to maintain a constant flow of irrigation fluid about a cutting end of the resecting tool.

Pneumatically-powered surgical tools with irrigation attachments often utilize independent valves in order to variably control the motor and the flow of irrigation fluid. The irrigation fluid is controlled separately from the motor. A surgical tool system which simultaneously operates the motor and the flow of irrigation fluid is desirable.

DISCLOSURE OF INVENTION

A surgical tool for resecting bone has a pneumatic motor within a tool body which rotates a coaxial tool implement. The tool implement is provided with irrigation fluid from a fluid reservoir. The reservoir and the motor are charged with pressurized air from a pressurized air source. A fluid control valve is located between the reservoir and the tool, and an air control valve is located between the air pressure source and the motor. The air control valve is controlled by a variable foot pedal or hand valve so that the speed of the motor is variably actuated by the foot valve.

BEST MODE FOR CARRYING OUT THE INVENTION

Figure 1:
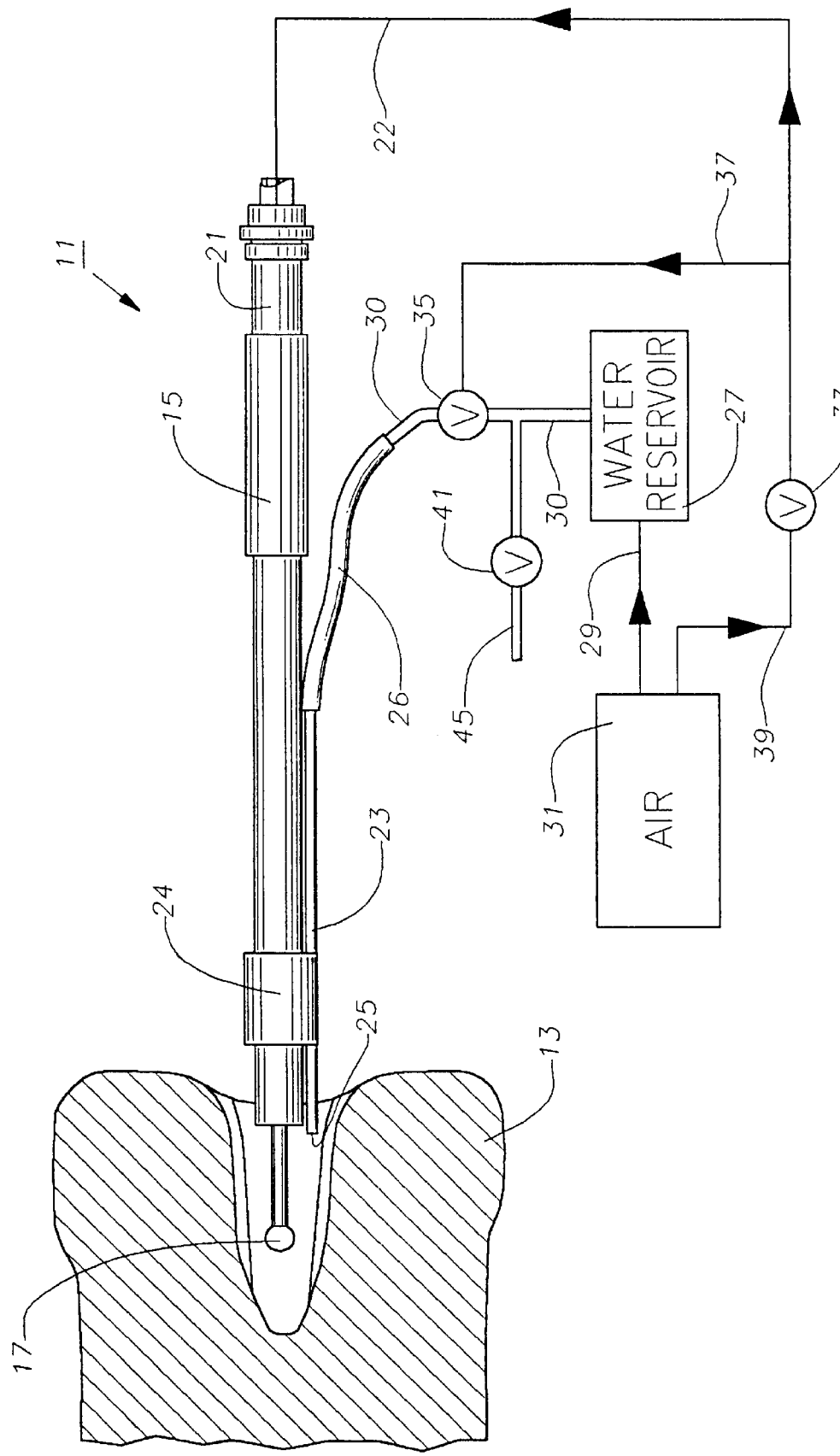
FIG. 1 is a schematic drawing of an irrigation pressurization system constructed in accordance with the invention.

Referring to FIG. 1, a surgical tool 11 of the present invention for resecting bone 13 is shown. Tool 11 has a tool body 15 which may be used to grip tool 11 and a coaxial tool implement 17 extending from a forward end thereof. Tool 11 has a pneumatic motor 21 for rotating implement 17. Pneumatic motor 21 is supplied with pressurized air between 20 and 200 psi through an air line 22 at a rearward end of tool 11.

Tool 11 also has means for providing a supply of irrigation fluid or saline solution near the end of implement 17. A flow passage or tube 23 is secured to body 15 along its length with a clip 24. Tube 23 has a discharge port 25 at its forward or specimen end near bone 13. Tube 23 provides an intermittent or continuous stream of fluid from a fluid/saline supply reservoir 27 when tool 11 is in use. Reservoir 27 may comprise a sealed bottle which is pressurized by air pressure, or a flexible bag which is pressurized by an inflatable bladder. A flexible fluid line 30 extends between reservoir 27 and tube 23. Reservoir 27 is charged with pressurized air from a pressurized air source 31. An air pressure line 29 having a regulator (not shown) extends between air pressure source 31 and reservoir 27. Fluid line 30 contains a secondary or fluid control valve 35 (shown schematically) located between reservoir 27 and tube 23. Valve 35 is a pneumatically actuated pilot valve which opens and closes fluid line 30 in response to air pressure.

Air line 22 contains a variable main or air control valve 33 located between air pressure source 31 and motor 21. An air pilot line 37 connects air hose 22 with valve 35. An air line 39 extends between air supply 31 and valve 33. In the preferred embodiment, valve 33 comprises a remotely operated foot pedal valve which is controlled by the foot of the user of tool 11.

A separate fluid dispensing hose 45 for manual use extends from hose 30 through a fluid dispensing valve 41. Valve 41 manually controls the amount of fluid released from hose 45.

In operation, the user holds tool 11 to position implement 17 near the work site on bone 13. Air source 31 supplies air pressure to tool 11 which is variably actuated by valve 33 in terms of the speed of motor 21. Opening valve 33 causes air to be supplied to motor 21. At the same time, valve 33 supplies air pressure to valve 35, causing it to open. Air pressure supplied to reservoir 27 causes saline solution to flow through tube 23 at a constant rate. The supply of fluid is constant regardless of the speed of motor 21. For example, when valve 33 is slightly depressed or opened, motor 21 will rotate implement 17 more slowly while a greater degree of opening of valve 33 results in motor 21 rotating implement 17 at a greater speed. When the user closes foot valve 33, valve 35 automatically stops the flow of irrigation fluid and motor 21 stops rotating implement 17. Physicians and assistants may irrigate manually at any time with hose 45 by manually opening valve 41. This can be done whether or not valve 33 is open.

The invention has several advantages. The irrigation fluid is simultaneously actuated with the operation of the motor. The tool speed may be varied while the irrigation flow remains constant.

Although the invention has been shown and described in only some of its forms, it should be apparent skilled in the art that it is not so limited but is susceptible to various changes without departing from the scope of the invention. For example, in the preferred embodiment, the tool is remotely operated by a foot valve which allows the user to retain the use of his hands for other requirements. Alternatively, the tool may be provided with a trigger-type valve on a pistol grip for controlling the flow of air and fluid.

I claim:

1. In a surgical tool having a tool implement rotated by a pneumatic motor and an irrigation fluid passage located adjacent to the tool implement, the improvement comprising:

an air hose connected to the motor and adapted to be connected to a pressurized air source;

a reservoir for containing irrigation fluid, the reservoir adapted to be pressurized by the air source;

an irrigation fluid line connected between the reservoir and the fluid passage; and control means for automatically causing fluid to flow through the fluid passage when air pressure is supplied to the motor and interrupting fluid flow through the fluid passage when air pressure ceases to be supplied to the motor.

2. The surgical tool of claim 1 wherein the control means comprises:

a manually operated main valve connected to the air hose for varying air flow to the motor;

a pneumatically actuated secondary valve connected to the fluid line for dispensing fluid through the fluid passage; and an air line connected from the secondary valve to the air hose downstream of the main valve for delivering air pressure to the secondary valve to cause the secondary valve to open and close in unison with the main valve.

3. The surgical tool of claim 1 wherein the control means is located remotely from the tool.

4. The surgical tool of claim 2 wherein the main valve is a variable foot pedal valve which is adapted to be controlled by an operator's foot.

5. The surgical tool of claim 1 wherein the reservoir is a flexible bag; and further comprising:

a supply line connecting the air source to the bag for supplying pressurized air to the bag.

6. The surgical tool of claim 1 wherein the reservoir is a sealed bottle; and further comprising:

a supply line connecting the air source to the bottle for supplying pressurized air to the bottle.

7. The surgical tool of claim 1, further comprising:

a dispensing hose extending from the reservoir; and a dispensing valve in the dispensing hose which is operable independently of the control means for controlling the flow of fluid out of the dispensing hose regardless of whether irrigation fluid is flowing out of the flow passage.

8. In a surgical tool having a tool implement rotated by a pneumatic motor and an irrigation fluid passage located adjacent to the tool implement, the improvement comprising:

an air hose connected to the motor and adapted to be connected to a pressurized air source;

a manually operated main valve connected to the air hose for varying air flow through the hose to the motor;

a reservoir for containing irrigation fluid and being pressurized by the air source;

an irrigation fluid line connected between the reservoir and the fluid passage;

a pneumatically actuated secondary valve connected into the fluid line for dispensing fluid through the fluid passage; and an air line connected from the secondary valve to the air hose downstream of the main valve for delivering air pressure to the secondary valve to cause the secondary valve to open and close in unison with the main valve.

9. The surgical tool of claim 8 wherein the main valve is located remotely from the tool implement.

10. The surgical tool of claim 8 wherein the main valve is actuated by a foot pedal.

11. The surgical tool of claim 8 wherein the reservoir is a flexible bag; and further comprising:

a supply line connecting the air source to the bag for supplying pressurized air to the bag.

12. The surgical tool of claim 8 wherein the reservoir is a sealed bottle; and further comprising:

a supply line connecting the air source to the bottle for supplying pressurized air to the bottle.

13. The surgical tool of claim 8, further comprising:

a dispensing hose extending from the reservoir; and a dispensing valve in the dispensing hose which is operable independently of the main valve for controlling the flow of fluid out of the dispensing hose regardless of whether irrigation fluid is flowing out of the flow passage.

14. A method for controlling a surgical tool having a tool implement rotated by a pneumatic motor and an irrigation fluid passage located adjacent to the tool implement, comprising:

(a) connecting an air hose between the motor and a pressurized air source to supply the motor with pressurized air;

(b) connecting an irrigation fluid reservoir to the fluid passage;

(c) connecting a fluid line between the reservoir and the air hose for pressurizing the reservoir with air pressure; and then (d) automatically causing fluid to be dispensed from the fluid passage when air pressure is delivered to the motor.

15. The method of claim 14, further comprising the step of controlling the flow of air pressure to the motor with a manually operated main valve.

16. The method of claim 14 further comprising the step of controlling the flow of irrigation fluid to the flow passage with a pneumatically operated secondary valve.

* * * * *